(12) United States Patent
Hasegawa

(10) Patent No.: US 7,172,419 B2
(45) Date of Patent: Feb. 6, 2007

(54) SUCTION TIP FOR DENTAL TREATMENT

(76) Inventor: Minako Hasegawa, 28-13 Higashimisono-cho, Tatebayashi-shi, Gunma (JP) 374-0031

( * ) Notice: Subject to any disclaimer, the term of this patent is extended or adjusted under 35 U.S.C. 154(b) by 0 days.

(21) Appl. No.: 11/358,129

(22) Filed: Feb. 22, 2006

(65) Prior Publication Data
US 2006/0204925 A1 Sep. 14, 2006

(30) Foreign Application Priority Data
Mar. 8, 2005 (JP) ............... 2005-063312

(51) Int. Cl.
A61C 17/06 (2006.01)
(52) U.S. Cl. ....................................... 433/91
(58) Field of Classification Search ............. 433/90–96
See application file for complete search history.

(56) References Cited

U.S. PATENT DOCUMENTS

| | | | | |
|---|---|---|---|---|
| 4,342,315 A | * | 8/1982 | Jackson | 604/35 |
| 5,114,342 A | * | 5/1992 | Young et al. | 433/95 |
| 5,941,703 A | * | 8/1999 | Van | 433/95 |
| 6,649,147 B1 | * | 11/2003 | Ye et al. | 424/49 |
| 2002/0177582 A1 | * | 11/2002 | Maloney | 514/182 |
| 2005/0096608 A1 | * | 5/2005 | Mannschedel et al. | 604/264 |

FOREIGN PATENT DOCUMENTS

| | | |
|---|---|---|
| JP | 58-124117 | 8/1983 |
| JP | 6-36616 | 5/1994 |
| JP | 2004-321710 | 11/2004 |
| JP | 2005-13394 | 1/2005 |

* cited by examiner

Primary Examiner—Cary E. O'Connor
(74) Attorney, Agent, or Firm—Morrison & Foerster LLP

(57) ABSTRACT

The invention provides a suction tip for dental treatment which has no possibility of causing a patient discomfort such as pain when its end portion touches the gingiva or oral cavity mucosa of the patient, and enables an easy suction operation and an easy attachment operation to a suction tube by its secured entire strength. The suction tip for dental treatment has a cylindrical shape as a whole, a front end portion of the cylinder is cut obliquely, and a back end portion thereof is cut vertically, thereby forming a back end opening portion and a front end opening portion. A front end portion which is to touch the gingiva or oral cavity mucosa of a patient is made of soft silicone rubber, and a cylindrical base portion continuing to this front end portion is made of hard silicone rubber. The soft silicone rubber forming the front end portion is gel silicone rubber.

8 Claims, 2 Drawing Sheets

SUCTION TIP FOR DENTAL TREATMENT

CROSS-REFERENCE OF THE INVENTION

This invention is based on Japanese Patent Application No. 2005-063312, the content of which is incorporated by reference in its entirety.

BACKGROUND OF THE INVENTION

1. Field of the Invention

The invention relates to a suction tip for dental treatment detachably attached to an end portion of a suction tube of a vacuum device.

2. Description of the Related Art

In dental treatment, a vacuum device is used for sucking saliva and so on in an oral cavity of a patient to remove these from the oral cavity. A cylindrical suction tip made of silicone rubber is attached to an end portion of a suction tube of the vacuum device so that the end portion of the suction tube does not directly touch the gingiva or oral cavity mucosa of a patient.

The relevant technology is described in the Japanese patent application publications Nos. 2005-13394 and 2004-321710 and the Japanese utility model application publications Nos. sho 58-124117 and hei 6-36616.

However, although made of a rubber material such as silicone rubber, the conventional suction tip for dental treatment sometimes causes a patient discomfort such as an uncomfortable feeling or pain when its end portion touches the gingiva or oral cavity mucosa of the patient.

It is possible to use soft silicone rubber as a material of the suction tip for dental treatment, but this causes a problem that the entire strength of the suction tip reduces to cause it deformation easily, making a suction operation and an attachment operation to the suction tube difficult.

SUMMARY OF THE INVENTION

The invention provides a suction tip for dental treatment including a cylinder made of silicone rubber, wherein a cylindrical end portion is made of soft silicone rubber and a cylindrical base portion is made of hard silicone rubber.

With the suction tip for dental treatment of the invention, there is no possibility of causing a patient discomfort such as pain when its end portion touches the gingiva or oral cavity mucosa of the patient, and further the entire strength of the suction tip is secured to facilitate a suction operation or an attachment operation to a suction tube.

Furthermore, since a flavoring is added to soft silicone rubber forming the end portion of the suction tip for dental treatment, flavor spreads therefrom and relaxes a patient when the end portion touches the gingiva or oral cavity mucosa of the patient.

DETAILED DESCRIPTION OF THE INVENTION

Figure 1:
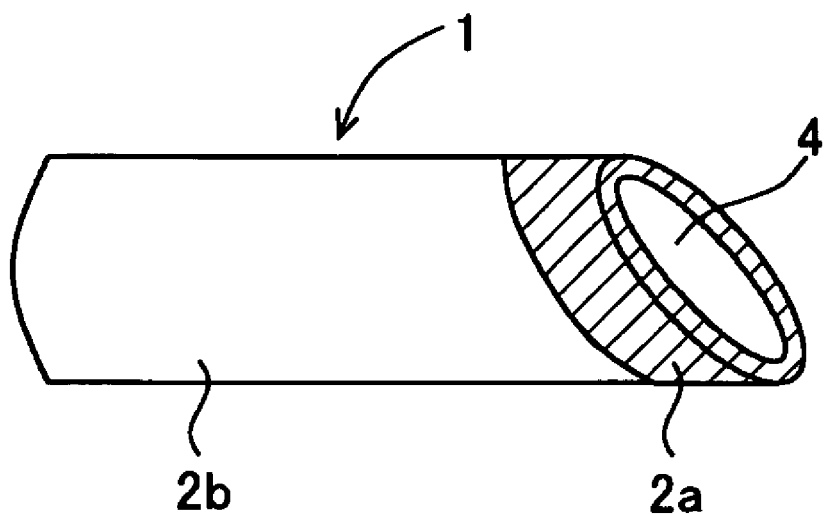
FIG. 1 is a perspective view of a suction tip for dental treatment of a first embodiment of the invention.
Figure 2:
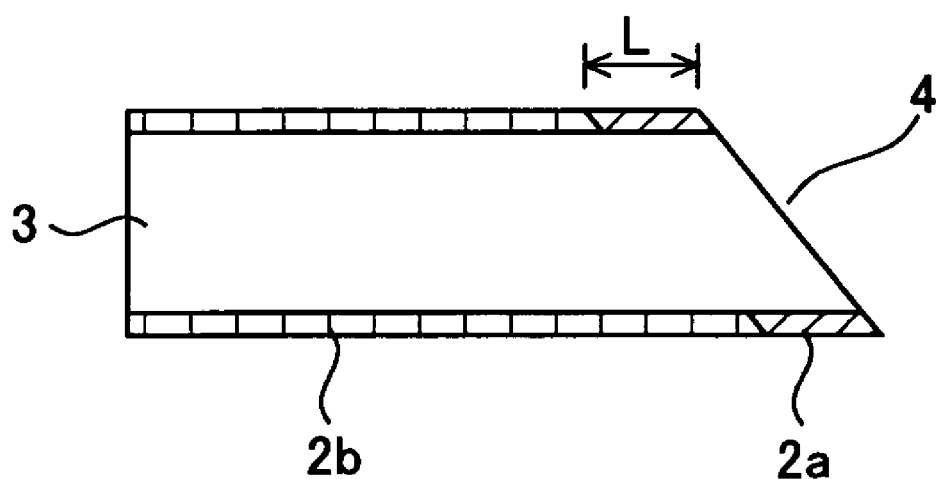
FIG. 2 is a cross-sectional view of the suction tip for dental treatment of the first embodiment of the invention along its longitudinal direction.

A suction tip for dental treatment of a first embodiment of the invention will be described with reference to FIGS. 1 and 2. FIG. 1 is a perspective view of this suction tip for dental treatment 1, and FIG. 2 is a cross-sectional view of the suction tip 1 along its longitudinal direction.

The suction tip for dental treatment 1 has a cylindrical shape as a whole, of which a front end portion of the cylinder is cut obliquely and a back end portion is cut vertically, forming a back end opening portion 3 and a front end opening portion 4. A front end portion 2a which is to touch the gingiva or oral cavity mucosa of a patient is made of soft silicone rubber, and a remaining cylindrical base portion 2b continuing to this front end portion 2a is made of hard silicone rubber. The soft silicone rubber forming the front end portion 2a is gel (jellied) silicone rubber, and its penetration index is 80 to 90 mm, preferably.

The hardness of the silicone rubber can be measured by a penetration test. The penetration test is a test where a metal cone of JIS (Japanese Industrial Standards) K2220 is used, a peak thereof is placed on a sample from above, and the penetration depth of the cone into the sample is measured. This depth is used as the penetration index. The larger this penetration index is, the softer the silicone rubber is.

In the invention, the front end portion 2a is made of soft silicone rubber, so that there is little possibility of causing a patient discomfort such as pain when the front end portion 2a touches the gingiva or oral cavity mucosa of the patient. Furthermore, although a suction tube of a vacuum device is to be inserted into the suction tip for dental treatment 1 from the back end opening portion 3 to the middle of the length of the suction tip 1, the cylindrical base portion 2b to be inserted with the suction tube is made of hard silicone rubber and thus has enough strength, thereby facilitating the attachment operation of the suction tip for dental treatment 1.

Furthermore, by adding a flavoring to the soft silicone rubber forming the front end portion 2a, flavor spreads therefrom and relaxes a patient when the front end portion 2a touches the gingiva or oral cavity mucosa of the patient. Type of the flavoring includes a mint flavoring, or a strawberry flavoring or a banana flavoring for a child, for example, and a patient can select one from them according to preference.

In a case of disinfecting the suction tip for dental treatment 1 by heat, there is a possibility of losing some of the flavoring to lighten the flavor. Therefore, it is possible to use the suction tip for dental treatment 1 sprayed with a flavoring after the heat disinfection.

Furthermore, adding a sweetening to the soft silicone rubber forming the front end portion 2a also has an effect of relaxing a patient. Xylitol is suitable as the sweetening. Xylitol is a sugar alcohol, and formed by processing a white birch or a core of a corn. The sugar alcohol includes many, i.e. sorbitol, maltitol, and erythritol, all of which are the sweetenings which do not cause dental caries.

The length of this suction tip for dental treatment 1 is about 40 to 50 mm, but it is preferable for practical use that the length L of the front end portion 2a is about 5 mm.

Figure 3:
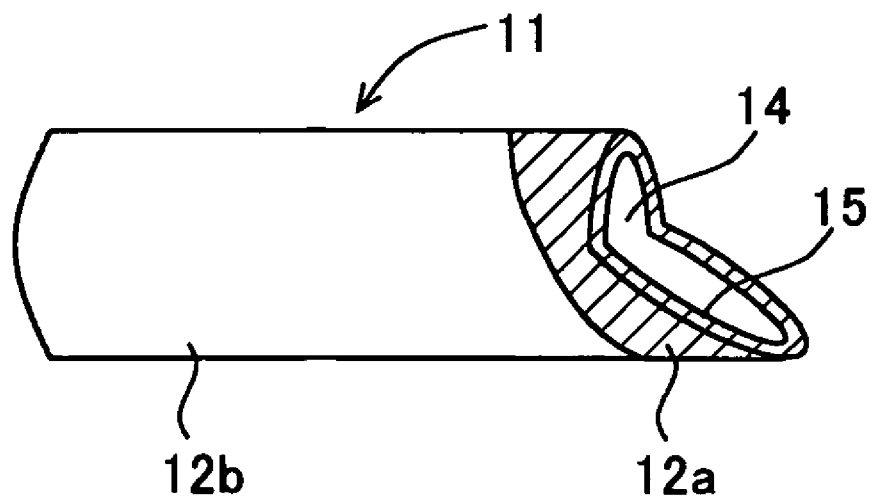
FIG. 3 is a perspective view of a suction tip for dental treatment of a second embodiment of the invention.
Figure 4:
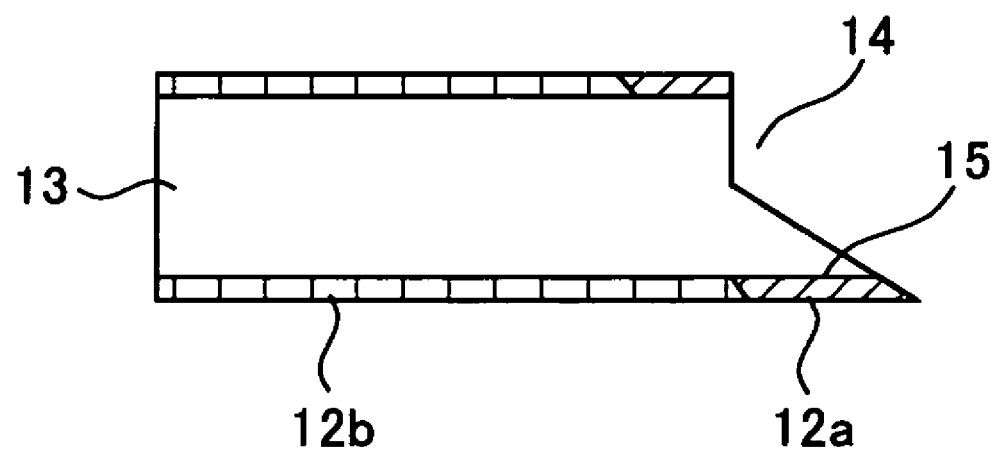
FIG. 4 is a cross-sectional view of the suction tip for dental treatment of the second embodiment of the invention along its longitudinal direction.

Next, a suction tip for dental treatment of a second embodiment of the invention will be described with reference to FIGS. 3 and 4. FIG. 3 is a perspective view of this suction tip for dental treatment 11, and FIG. 4 is a cross-sectional view of the suction tip 11 along its longitudinal direction.

This suction tip for dental treatment 11 is also a cylindrical tube, and has a back end opening portion 13 and a front end opening portion 14. A front end portion 12a which is to touch the gingiva or oral cavity mucosa of a patient is made of soft silicone rubber, and a cylindrical base portion 12b other than the front end portion 12a is made of hard silicone rubber.

This suction tip for dental treatment 11 differs from the one of the first embodiment in that an extended portion 15 extending from an edge of the front end opening portion 14 like a tongue is formed. Since mainly this extended portion 15 touches the gingiva or oral cavity mucosa of a patient, the front end portion 12a including this extended portion 15 is made of soft silicone rubber.

What is claimed is:

1. A suction tip for dental treatment, comprising:
    a cylindrical base portion made of a first silicone rubber and configured to receive a suction tube; and
    a cylindrical end portion cut obliquely and made of a second silicone rubber, the cylindrical end portion being permanently connected with the cylindrical base portion,
    wherein a penetration index of the second silicone rubber is larger than a penetration index of the first silicone rubber.
2. The suction tip for dental treatment of claim 1, wherein the second silicone rubber is a gel silicone rubber.
3. The suction tip for dental treatment of claim 1, wherein the penetration index of the second silicone rubber is 80–90 mm.
4. The suction tip for dental treatment of claim 1, wherein a flavoring is added to the second silicone rubber.
5. The suction tip for dental treatment of claim 4, wherein the flavoring is either a mint flavoring, a strawberry flavoring, or a banana flavoring.
6. The suction tip for dental treatment of claim 1, wherein a sweetening is added to the second silicone rubber.
7. The suction tip for dental treatment of claim 6, wherein the sweetening is xylitol.
8. The suction tip for dental treatment of claim 1, further comprising a layer of a flavoring sprayed on the cylindrical base portion and the cylindrical end portion.

* * * * *